United States Patent
Yamazaki et al.

(10) Patent No.: US 6,572,637 B1
(45) Date of Patent: Jun. 3, 2003

(54) HANDBREADTH-SIZED LASER BEAM PROJECTING PROBE FOR BEAUTY TREATMENT

(75) Inventors: Iwao Yamazaki, Tokyo (JP); Yoshihiro Izawa, Tokyo (JP)

(73) Assignee: Ya-Man Ltd., Tokyo (JP)

( * ) Notice: Subject to any disclaimer, the term of this patent is extended or adjusted under 35 U.S.C. 154(b) by 0 days.

(21) Appl. No.: 09/520,211

(22) Filed: Mar. 7, 2000

(30) Foreign Application Priority Data

Mar. 12, 1999 (JP) .......................................... 11-067334

(51) Int. Cl.[7] .............................................. A61N 5/067
(52) U.S. Cl. ................................ 607/89; 607/88; 606/9
(58) Field of Search ................................ 606/9; 607/89

(56) References Cited

U.S. PATENT DOCUMENTS

| | | | | |
|---|---|---|---|---|
| 5,325,678 A | * | 7/1994 | Borah et al. .................. | 62/126 |
| 5,464,436 A | * | 11/1995 | Smith ........................... | 607/89 |
| 5,553,629 A | * | 9/1996 | Keipert et al. ................ | 606/13 |
| 5,616,140 A | * | 4/1997 | Prescott ........................ | 606/10 |
| 5,628,744 A | * | 5/1997 | Coleman et al. .............. | 606/12 |
| 5,830,211 A | * | 11/1998 | Santana et al. ............... | 606/27 |
| 5,928,220 A | * | 7/1999 | Shimoji ......................... | 606/2 |
| 5,989,245 A | * | 11/1999 | Prescott ........................ | 606/14 |
| 6,033,431 A | * | 3/2000 | Segal ............................ | 606/89 |
| 6,066,129 A | * | 5/2000 | Larson .......................... | 606/10 |
| 6,096,029 A | * | 8/2000 | O'Donnel, Jr. ................ | 606/9 |
| 6,334,074 B1 | * | 12/2001 | Spertell ........................ | 606/31 |

* cited by examiner

*Primary Examiner*—Linda C. M. Dvorak
*Assistant Examiner*—Henry M. Johnson

(57) ABSTRACT

A handbreadth-sized laser beam projecting probe for beauty treatment, comprising: a semiconductor laser device for producing a laser beam; a drive circuit for driving the semiconductor laser device; a heat sink for removing the generated heat from the semiconductor laser device; a CPU for controlling the radiation of the laser beam from the semiconductor laser device; a condenser lens for condensing the laser beam from the semiconductor laser device; an adjuster for adjusting the distance between the skin and the condenser lens; and an on-and-off switch associated with an electric power supply. The handbreadth-sized probe can be carried everywhere, permitting the practice of beauty treatment when desired.

9 Claims, 3 Drawing Sheets

HANDBREADTH-SIZED LASER BEAM PROJECTING PROBE FOR BEAUTY TREATMENT

BACKGROUND OF THE INVENTION

Field of the Invention

The present invention relates to a handbreadth-sized laser projecting apparatus for beauty treatment in which a laser beam is thrown to a selected skin part of the human body.

A beauty treatment for the purpose of improving the body shape, the skin appearance, hair removal or growth must be continued for an elongated length of time. The laser projecting probe if separated from the beauty treatment apparatus to be carried, will conveniently permit practice of a required beauty treatment everywhere.

To attain this it is necessary that the probe be reduced in size and weight, and that the laser, control, console, indicators and other associated parts be shifted from the beauty treatment apparatus to the probe. Also, it is required that the probe be held in one hand, and be handled with a selected finger in operation, as for instance, the following: the switch is a push-button switch rather than a rotary or toggle switch, and is so positioned that a selected finger or fingers may be accessible to the switch; one and the same switch is responsive to different predetermined lengths of time for which the switch is continuously pushed for selecting different modes of operation; and LEDs give indications of different working modes in terms of colors and/or flashes of light.

SUMMARY OF THE INVENTION

One object of the present invention is to provide a handbreadth-sized laser beam projecting probe for beauty treatment capable of control with a selected finger or fingers while being held in one hand.

To attain this object a laser beam projecting probe according to the present invention comprises: a semiconductor laser device for producing a laser beam; a drive circuit for driving the semiconductor laser device; a heat sink for remove the generated heat from the semiconductor laser device; a CPU for controlling the radiation of the laser beam from the semiconductor laser device; a condenser lens for condensing the laser beam from the semiconductor laser device; an adjuster for adjusting the distance between the skin and the condenser lens for focussing the laser beam on the skin; and an on-and-off switch associated with an electric power supply.

The CPU may control the semiconductor laser device so as to project the laser beam intermittently at a fixed on-and-off cycle.

The "on"-time of the fixed on-and-off period can be varied step by step with the aid of switching means.

The switching means may be the on-and-off switch associated with the electric power supply.

The first push of the on-and-off switch may put the electric power supply in circuit; the second and subsequent pushes of the on-and-off switch change the "on"-time of the fixed on-and-off period incrementally; and the final push of the on-and-off switch removes the electric power supply from the circuit.

The incremental change of the "on"-time of the fixed on-and-off period may include three or more sequential steps at which the "on"-time is elongated longer and longer.

The laser beam projecting probe may comprise further a single LED lamp for indicating at which step of "on"-time the laser beam projector works.

The single LED lamp comprises a plurality of LED elements of different colors, in terms of whic colors a required indication is given.

A required indication may be given by intermittent flashing of all of or selected one or ones of the LED elements.

The switch associated with the electric power supply may be so positioned that a selected finger may be conveniently accessible to the switch while holding the probe in hand.

The switch associated with the electric power supply may be fixed to the adjuster for detecting the touch of the probe on the skin.

Other objects and advantages of the present invention will be understood from the following description of a handbreadth-sized laser beam projecting probe for beauty treatment according to one preferred embodiment of the present invention, which is shown in accompanying drawings:

DESCRIPTION OF PREFERRED EMBODIMENTS

Figure 1:
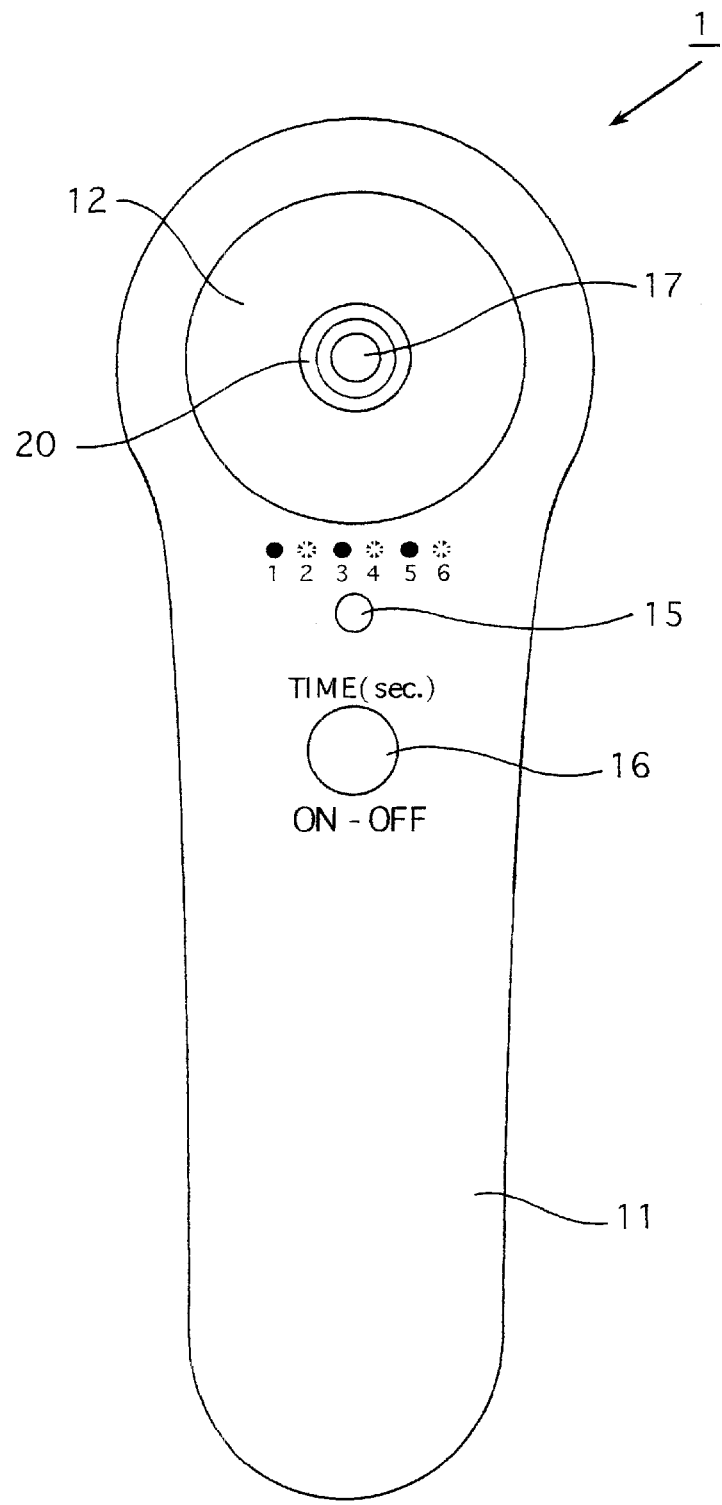
FIG. 1 is a front view of a handbreadth-sized laser beam projecting probe for beauty treatment according to one preferred embodiment of the present invention.
Figure 2:
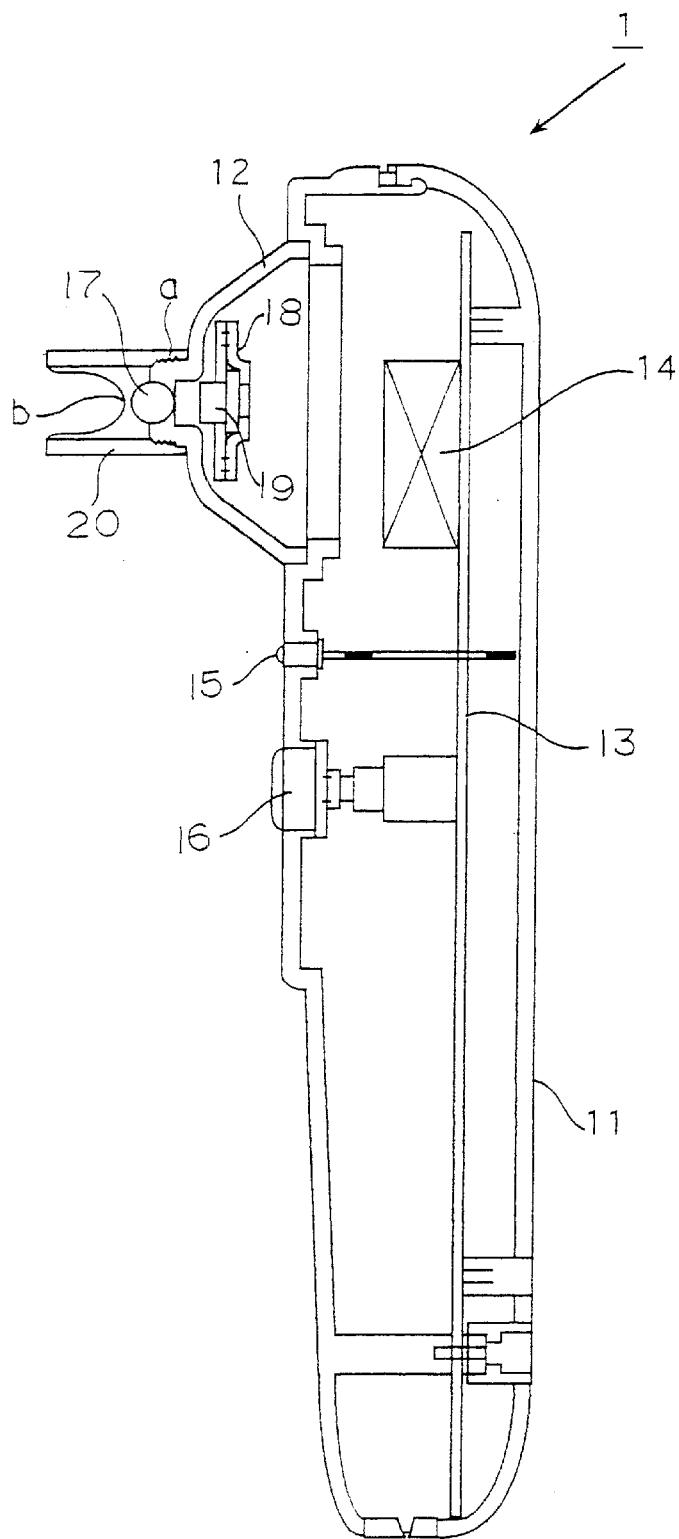
FIG. 2 is a longitudinal section of the handbreadth-sized laser beam projecting probe.

Referring to FIGS. 1 and 2, a handbreadth-sized laser beam projecting probe 1 according to the present invention includes a casing 11 having a frustoconical head 12 projecting from its upper front. The casing 11 has a base plate 13 fixed inside. On the base plate 13 there are a control circuit, a semiconductor laser device (not shown), a fan 14, an LED lamp 15 and a push-button switch 16. The control circuit uses a timer for controlling the "on"-time for which the semiconductor laser device is allowed to produce a laser beam. The LED lamp 15 is composed of red and green LED chips to produce three different colored beams, that is, red, green and amber by energizing the red LED chip alone, the green LED chip alone and both LED chips together.

The fan 14 is positioned behind the frustoconical head 12 for cooling the parts installed therin. The push-button switch 16 and the LED chips 15 partly appear in the small openings made on the front side of the casing 11.

As seen from FIG. 2, the frustconical head 12 has a spherical lens 17 fitted in its center opening, and a heat sink 18 is positioned close to the ceiling of the head 12. The semiconductor laser diode 19 is put in alignment with the optical axis of the spherical lens 17, and is seated on the heat sink 18, which functions to remove the heat from the laser diode 19 during operation, thereby preventing its efficiency from being lowered. To conduct the generated heat efficiently the heat sink 18 is an aluminum or aluminum alloy casting, and it has through holes made therein for dissipating the heat.

The laser diode 19 is a P-N junction diode of GaAs or any other semiconductor compound. The laser diode 19 can be energized by making an electric current to flow therethrough to produce a laser beam.

Such a semiconductor laser device is small in size and light in weight, and is capable of oscillating at an increased efficiency. Still advantageously, it is responsive to application of a low voltage thereacross for producing a laser beam, thus permitting use of a battery for driving. It has a long life, and can be mass-produced and accordingly less expensive. For these reasons the semiconductor laser device is appropriate for use in a handbreadth-sized laser beam projecting probe.

The spherical lens seat has spiral male-threads "a" formed on its outer circumference. Likewise, a cylindrical adjuster 20 has spiral female-threads formed inside, and is attached to the frustoconical head 12 by threadedly engaging with the spherical lens seat.

The cylindrical adjuster 20 is made of a transparent acrylic resin, thus permitting the laser spot to be visible from the outside. The cylindrical adjuster 20 has a notch "b" made in the vicinity of the open end for ventilation.

The distance from the skin to the spherical lens 17 can be adjusted by rotating the cylindrical adjuster 20 about the spherical lens seat.

The push-button switch 16 can effect the on-and-off control of an electric power supply, and can change the length of time for intermittent radiation of laser beams.

The adjuster 20 may be equipped with an extra microswitch responsive to adjuster's touching the skin for making the electric power supply to turn on, and responsive to adjuster's leaving the skin for making the electric power supply to turn off. Thus, radiation of laser beams is not permitted when the adjuster 20 is apart from the skin, and thereafter, there is no fear for inadvertently allowing the laser beam to be thrown in anyone's eyes.

Figure 3:
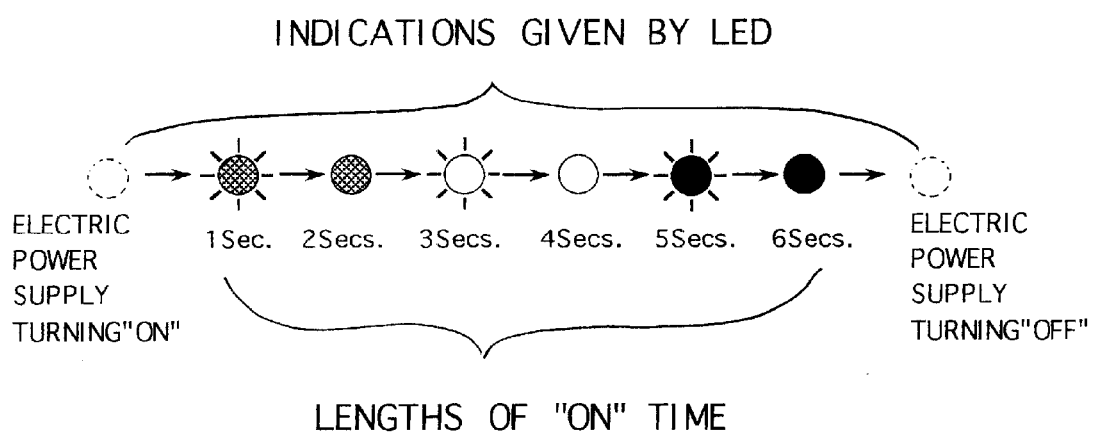
FIG. 3 illustrates how LED elements indicate different lengths of "on"-time.

Referring to FIG. 3, the first push of the push-button switch 16 makes the electric power supply to turn on; the second and subsequent pushes of the push-button switch 16 sequentially change the "on"-time (laser radiation time) to be one second, two seconds, three seconds, four seconds, five seconds and six seconds long; and the final, seventh push of the push-button switch makes the electric power supply to turn off. On the other hand, the LED lamp 15 changes its color from green to flickering red through flickering green, amber, flickering amber and red to indicate the sequential elongation of the "on"-time from one to six seconds long. Finally the push-button switch 16 is depressed a relatively long time, say, 1.5 seconds long to make the electric power supply to turn off, thus stopping the laser radiation.

The setting of sequentially elongated "on"-time permits appropriate amount of laser radiation to be selected, thereby preventing any damage to be caused on the skin.

In practicing a desired beauty treatment with the handbreadth-sized laser projecting probe, first, the push-button switch 16 is pushed to make the electric power supply to turn on.

Then, the laser diode 19 projects a laser beam every other second. When it is desired that the length of intermittent radiation is changed, the pushing of the push-button switch 16 is continued until the desired "on"-time indication appears, and then the push-button switch 16 is released, thereby permitting the laser beam to be projected at the desired cycle.

The skin is exposed to the laser beam while the adjuster 20 is pushed against the skin, and the probe is moved on the skin for treatment.

The laser beam can be focused on the skin by rotating the adjuster 20.

As may be understood from the above, a handbreadth-sized laser beam projecting probe has all pats required for producing a laser beam installed therein, and the probe has a console and indicators provided on its front. The handbreadth-sized probe can be carried everywhere, thus permitting the practice of beauty treatment when desired. The length of "on"-time (or laser radiation) can be selectively determined by changing the length of time for which one and same push-button switch is continued to be pushed. All control required for a desired beauty treatment can be effected simply by pushing the single push-button switch with a selected finger while the handbreadth-sized probe is held in one hand.

Every time the push button switch has been depressed a controlled length of time, the "on"-time may be extended incrementally, and therefore, the user can easily determine which "on"-time is most appropriate for treatment from the sensibility of the skin exposed to the laser beam.

A single LED lamp permits indication of three or more different "on"-time treatments, thus facilitating the observing of treatment conditions by sight. Advantageously the LED lamp is simple in structure, and less expensive.

What is claimed is:

1. A handbreadth-sized laser beam projecting probe for beauty treatment, comprising:

a semiconductor laser device for producing a laser beam;

a drive circuit for driving the semiconductor laser device;

a heat sink for removing a generated heat from the semiconductor laser device;

a CPU for controlling radiation of the laser beam from the semiconductor laser device;

a condenser lens for condensing the laser beam from the semiconductor laser device;

an adjuster for adjusting a distance between a skin and the condenser lens;

a microswitch associated with an electric power supply, said microswitch being fixed to said adjuster for detecting contact of said adjuster on an area to be treated, and a push button switch associated with said CPU, whereby sequential pushes of the push button switch incrementally vary the "on"-time of the semiconductor laser device; and a single LED lamp for indicating at which step of "on"-time the laser beam projector works.

2. A handbreadth-sized laser beam projecting probe for beauty treatment according to claim 1 wherein the CPU controls the semiconductor laser device so as to project the laser beam intermittently at a fixed on-and-off cycle.

3. A handbreadth-sized laser beam projecting probe for beauty treatment according to claim 1 wherein a first push of the push button switch puts the electric power supply in circuit; a second and subsequent pushes of the push button switch change the "on"-time; and a final push of the push button switch removes the electric power supply from the circuit.

4. A handbreadth-sized laser beam projecting probe for beauty treatment according to claim 3 wherein an incremental change of the "on"-time of the fixed on-and-off period includes three or more sequential steps at which the "on"-time is elongated longer and longer.

5. A handbreadth-sized laser beam projecting probe for beauty treatment according to claim 1 wherein the single LED lamp comprises a plurality of LED elements of different colors, in terms of which colors a required indication is given.

6. A handbreadth-sized laser beam projecting probe for beauty treatment according to claim 1 wherein a required indication is given by intermittent flashing of all of or selected one or ones of the LED elements.

7. A handbreadth-sized laser beam projecting probe for beauty treatment according to claim 1 wherein the push button switch associated with the electric power supply is so positioned that a selected finger may be conveniently accessible to the switch while holding the probe in hand.

8. A handbreadth-sized laser beam projecting probe for beauty treatment, comprising:

a semiconductor laser device for producing a laser beam;

a drive circuit for driving the semiconductor laser device;

a heat sink for removing a generated heat from the semiconductor laser device;

a CPU for controlling radiation of the laser beam from the semiconductor laser device;

a condenser lens for condensing the laser beam from the semiconductor laser device;

an adjuster for adjusting a distance between a skin and the condenser lens;

a microswitch associated with an electric power supply, said microswitch being fixed to said adjuster for detecting contact of said adjuster on an area to be treated, and a push button switch associated with said CPU, whereby sequential pushes of the push button switch incrementally vary the "on"-time of the semiconductor laser device; and a single LED lamp for indicating at which step of "on"-time the laser beam projector works, wherein:

a first push of said on-and-off switch puts the electric power supply in circuit, a second and subsequent pushes of the push button switch change the "on"-time of the fixed on-and-off period incrementally, and a final push of the push button switch removes the electric power supply from the circuit.

9. A handbreadth-sized laser beam projecting probe for beauty treatment according to claim 1, wherein:

said adjuster comprises a cylindrical adjuster which is rotated to effect said distance adjustment.

* * * * *